United States Patent
Godin

(10) Patent No.: US 10,085,867 B2
(45) Date of Patent: Oct. 2, 2018

(54) ANTI-REFLUX OR ANTI-OBESITY PROSTHESIS

(71) Applicant: BIOMEDIX S.A., Geneva (CH)

(72) Inventor: Norman Godin, Geneva (CH)

(73) Assignee: BIOMEDIX, Geneva (CH)

( * ) Notice: Subject to any disclaimer, the term of this patent is extended or adjusted under 35 U.S.C. 154(b) by 135 days.

(21) Appl. No.: 15/353,822

(22) Filed: Nov. 17, 2016

(65) Prior Publication Data

US 2017/0065445 A1 Mar. 9, 2017

Related U.S. Application Data

(62) Division of application No. 14/349,840, filed as application No. PCT/EP2012/069487 on Oct. 2, 2012, now Pat. No. 9,572,701.

(30) Foreign Application Priority Data

Oct. 5, 2011 (GB) .................................. 1117106.3
Oct. 2, 2012 (WO) ................. PCT/EP2012/069487

(51) Int. Cl.
| | | |
|---|---|---|
| A61F 5/00 | (2006.01) | |
| A61M 27/00 | (2006.01) | |
| A61B 1/273 | (2006.01) | |

(52) U.S. Cl.
CPC .......... *A61F 5/0076* (2013.01); *A61B 1/2733* (2013.01); *A61B 1/2736* (2013.01); *A61F 5/0089* (2013.01); *A61M 27/002* (2013.01); *A61F 2005/0016* (2013.01)

(58) Field of Classification Search
CPC .................................................... A61F 5/0076
See application file for complete search history.

(56) References Cited

U.S. PATENT DOCUMENTS

| | | | |
|---|---|---|---|
| 4,728,328 A | 3/1988 | Hughes | |
| 6,764,518 B2 | 7/2004 | Godin | |
| 2008/0065136 A1 | 3/2008 | Young | ........................ A61F 2/04 606/191 |
| 2008/0249533 A1 | 10/2008 | Godin | |

FOREIGN PATENT DOCUMENTS

| | | |
|---|---|---|
| FR | 2513111 A1 | 3/1983 |
| WO | WO2007/137228 A2 | 11/2007 |
| WO | WO 2008/028037 A2 | 3/2008 |

OTHER PUBLICATIONS

International Search Report and Written Opinion issued by EPO dated Dec. 19, 2012.
Hashem El-Serag, "The Association Between Obesity and GERD: a Review of the Epidemiological Evidence," Digestive Disease and Science, Sep. 2008, pp. 2307-2312, vol. 53(9).
Gluck B et al., "Laparoscopic sleeve gastrectomy is a safe and effective bariatric procedure for the lower BMI (35.0-43.0 kg/m2) population," Obes Surg., Aug. 2011, pp. 1168-1171, vol. 21(8).
Burgerhart JS et al., "Effect of Sleeve Gastrectomy on Gastroesophageal Reflux," Obes Sueg., Mar. 12, 2014.

*Primary Examiner* — Tatyana Zalukaeva
*Assistant Examiner* — Kai Weng
(74) *Attorney, Agent, or Firm* — Michael B. Fein; Eckert Seamans Cherin & Mellott, LLC

(57) ABSTRACT

A prosthesis (14) that is useful as an anti-reflux device or an anti-obesity device within a gastro-intestinal tract of a living organism, such as a human, comprises an elastic portion including a helical elastic spring (15) embedded in a biocompatible material.

11 Claims, 15 Drawing Sheets

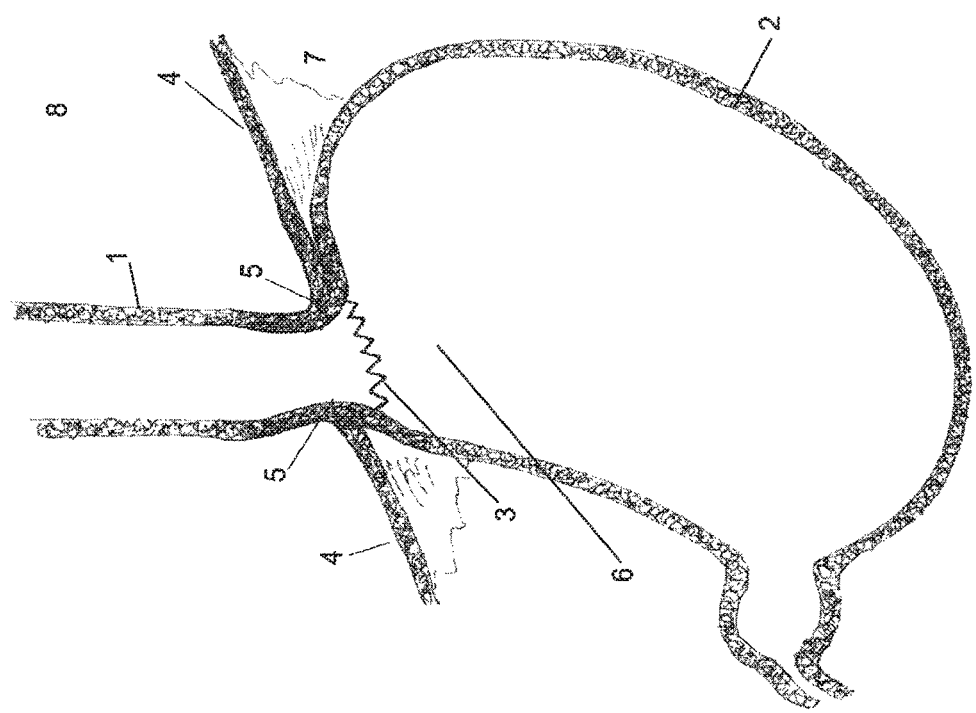

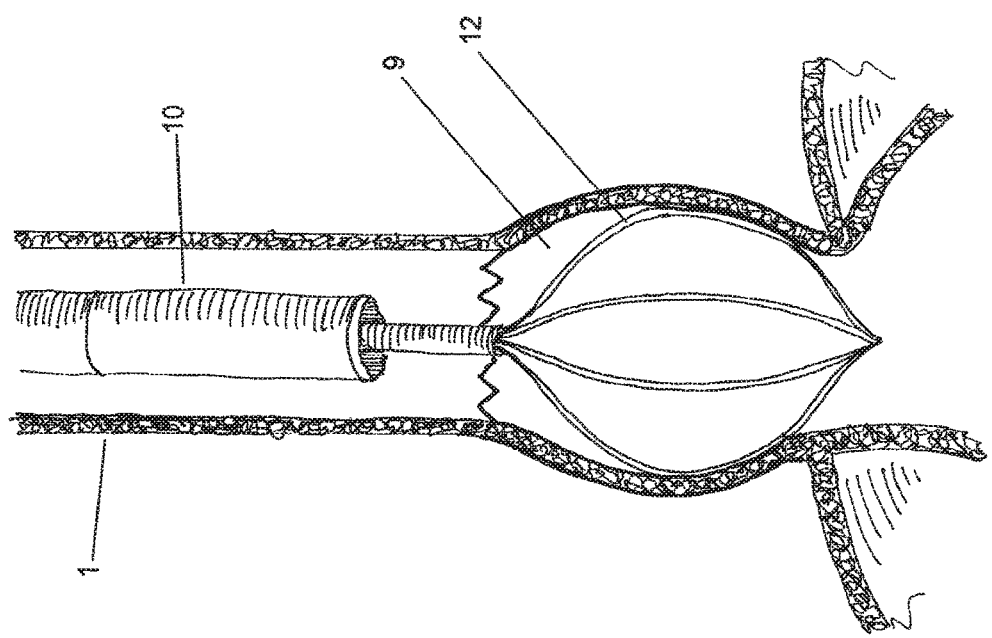

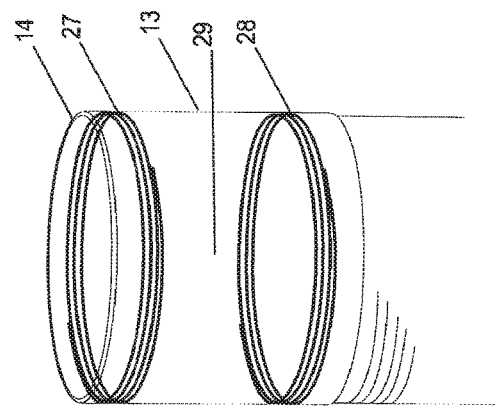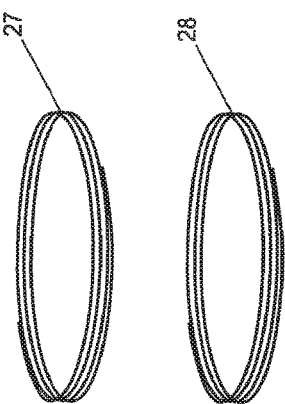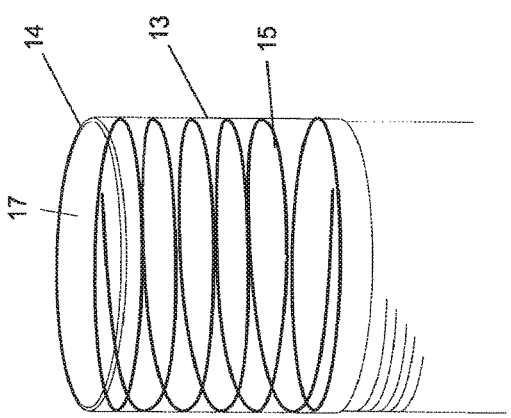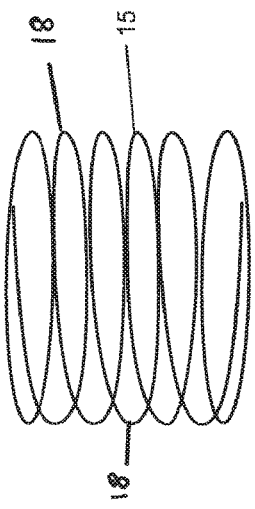

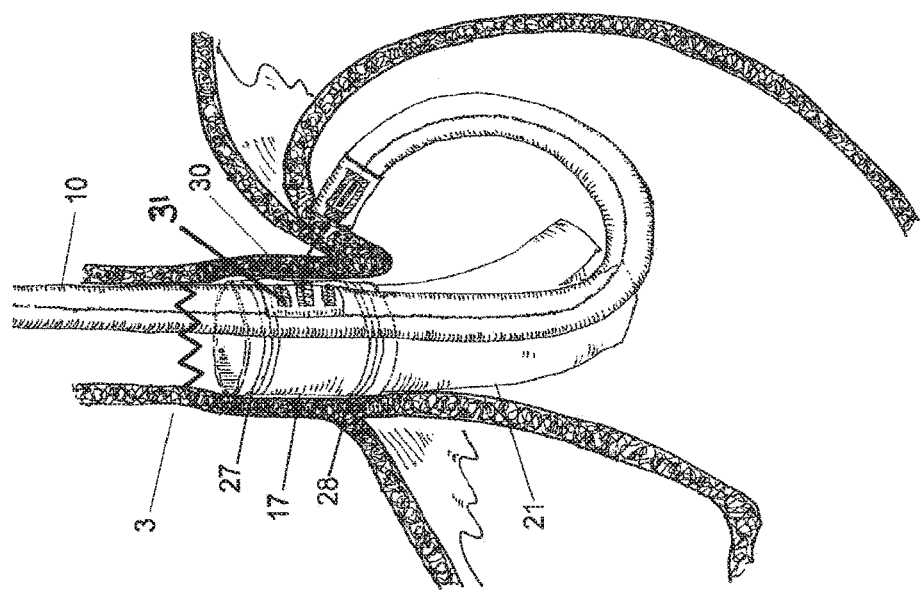
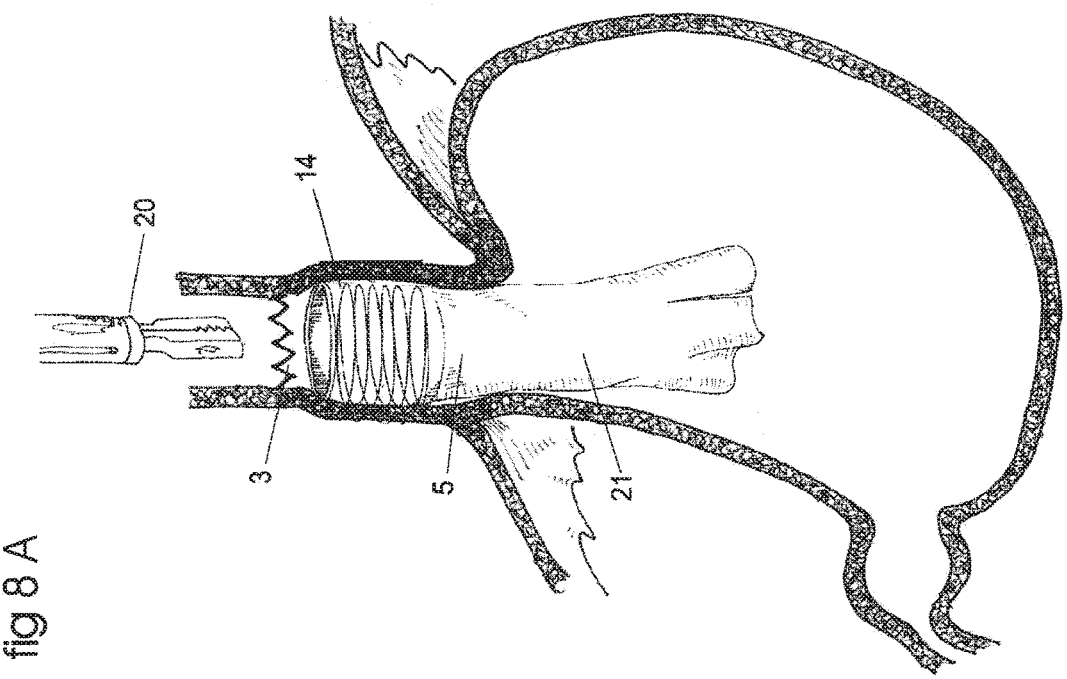

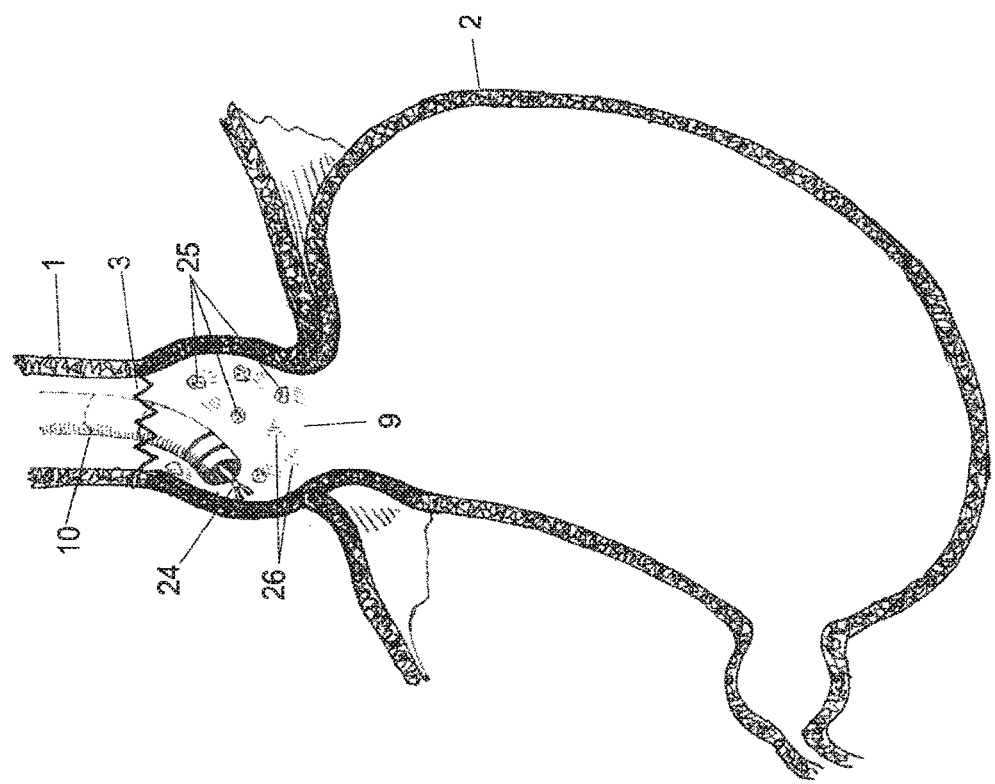

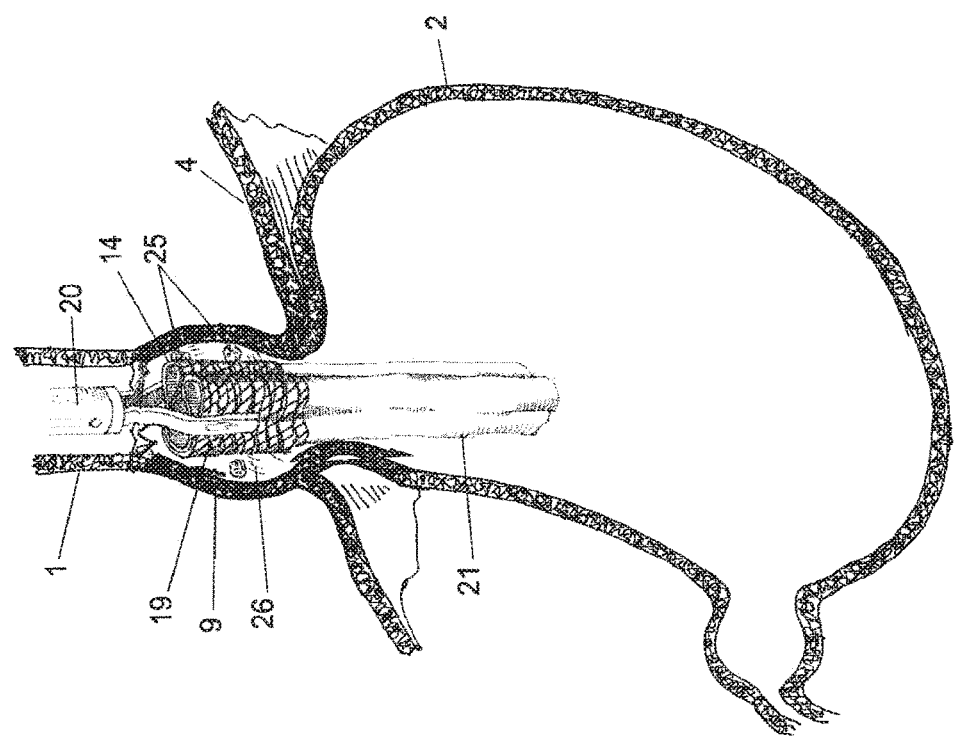

ANTI-REFLUX OR ANTI-OBESITY PROSTHESIS

CROSS-REFERENCE TO RELATED APPLICATIONS

This application is a Divisional of application Ser. No. 14/349,840, filed Apr. 4, 2014, which is in turn a national stage of International Application No. PCT/EP2012/0069487, filed Oct. 2, 2012, which claims the benefit of GB Patent Application Serial No, 1117106.3, filed Oct. 5, 2011, all of which are hereby incorporated by reference.

The present invention concerns a prosthesis and methods involving the use of said prosthesis. More particularly, the present invention concerns a prosthesis intended for use in the gastro-intestinal tract within a living organism, preferably a mammal such as a human, an endoscopic procedure for positioning such a prosthesis within the gastro-intestinal tract, a method of treating reflux disease using such a prosthesis and a method of reducing obesity using such a prosthesis.

BACKGROUND OF THE INVENTION

U.S. Pat. No. 6,764,518 describes a prosthesis, for controlling the direction of flow in the gastro-intestinal tract of a living organism e.g. a mammal, consisting of a hollow elongate body consisting of a proximal elastic portion, that provides an annular fixing part, comprising a relatively thick wall having inner and outer surfaces that together define a cylindrical tube, comprising an elastic spring, such as a meandering nitinol spring or split ring, that extends substantially the length of the elastic portion, embedded within a biocompatible plastics material, and, joined integrally thereto, a distal flexible portion comprising a relatively thin wall having inner and outer surfaces that together define a tube having a passageway and consisting of a biocompatible plastics material. When exposed to a distorting pressure, the elastic portion can be folded e.g. to assist conveyance of the prosthesis with an endoscope, but is capable of returning to its normal undistorted shape once the distorting pressure is removed. In use, the elastic portion at the proximal end of the prosthesis is located e.g. in the esophagus or hiatus hernia, and the flexible portion at the distal end of the prosthesis extends down the tract into e.g. the stomach or intestine. When an overpressure is exerted on its outer surface, the flexible portion collapses on itself, so blocking the passageway and thereby preventing back-flow, as seen in GERD or gastroesophageal reflux disease. A prosthesis of similar design but being relatively longer and provided with relatively thicker walls than the above anti-reflux tubes can be used to reduce obesity by slowing down the ingestion of food in the gastro-intestinal tract, thereby inducing satiety, as described in US 2008-0249533 A1.

A prosthesis of the above design may be positioned in the gastro-intestinal tract by locating the elastic portion of the prosthesis in the natural "cavity" created by a fixed or sliding hiatus hernia, as illustrated in FIG. 1B (9) at least 1 cm high and no more than 6 cm high measured from the Z line (3), which is the junction of the esophageal mucosa and the gastric mucosa and the hiatus (5) or orifice of the diaphragm (4) that can easily and readily be seen and measured by any gastroenterologist practicing endoscopy. It is also possible to locate a prosthesis of the above design in the gastro-intestinal tract without having a hernia creating a distended area with the elastic portion positioned in the lower esophagus above the Z line (3), as illustrated in FIG. 1A. The diameter of the hernia or lower esophagus is measured with a calibration basket (12) that can be passed through the working channel of a standard gastroscope (10), as illustrated in FIG. 2. The calibration basket will enable the diameter of the hernia or esophagus to be measured, which in turn will determine the size of the prosthesis to be placed in the patient. When the elastic portion is correctly located, the flexible portion of the prosthesis extends from the elastic portion down the tract and into the stomach, where it may terminate at its distal end.

An endoscopic procedure may be employed to position a prosthesis in the gastro-intestinal tract. For example, a prosthesis having an elastic portion comprising a meandering nitinol spring, such as illustrated in FIG. 3 of U.S. Pat. No. 6,764,518 may be fitted by a procedure that typically comprises tightly folding the elastic portion and conveying the prosthesis with the endoscope, through the mouth and down the esophagus, where the prosthesis is released from the endoscope at or near to the position where the prosthesis is to be located. Releasing the elastic portion enables it to unfold and resume its normal undistorted shape in the gastro-intestinal tract. The prosthesis can be finally positioned, e.g. with the elastic portion located in the lower esophagus or hiatus hernia and the flexible portion extending down the tract into the stomach.

Once positioned in the gastro-intestinal tract, a prosthesis having an elastic portion comprising a meandering nitinol spring can be exposed to significant peristaltic movements that may push the prosthesis lower down the gastro-intestinal tract e.g. from the esophagus or hiatus hernia into the stomach or even further down into the intestinal tract.

To reduce the problem of the prosthesis becoming dislodged from its correct position within the gastro-intestinal tract, the meandering spring may be replaced by a split ring that extends substantially the length of the elastic portion, such as illustrated in FIG. 4 and FIG. 5 of U.S. Pat. No. 6,764,518. However, whilst such a prosthesis is less susceptible to being dislodged from its correct position by peristaltic forces, the continuous pressure exerted by the ring on the mucosal wall can cause local granulation (proliferation of tissue) that can occlude the prosthesis around the ring and/or cause bleeding ulcerations in the mucosal wall of the hernia.

The object of the present invention is to provide a prosthesis, consisting of hollow elongate body consisting of an elastic portion and a flexible portion, that is no more difficult to fit in position in the gastro-intestinal tract than the prostheses disclosed in U.S. Pat. No. 6,764,518 but which is less prone to displacement from its fitted position by peristaltic pressure than the prosthesis having an elastic portion comprising a meandering elastic spring and which is less prone to cause local granulation and/or ulceration that the prosthesis having an elastic portion comprising a slit ring.

SUMMARY OF THE INVENTION

The invention, in its various aspects, is as set out in the accompanying claims.

In accordance with a first aspect of the present invention, there is provided a prosthesis for use as an anti-reflux device or anti-obesity device within gastro-intestinal tract of a living organism, said tract Comprising an entrance end, an exit end and a wall defining a passageway, of generally circular cross-section having a diameter, along which compositions such as masticated food, digestive secretions and/or mixtures thereof are conveyed within the living organism in a direction towards the exit end of the tract; said prosthesis consisting of a hollow elongate body, having a proximal end and a distal end, wherein said hollow elongate body consists of:

a) an elastic portion having a normal undistorted shape comprising a wall having an inner surface and an outer surface that together define cylindrical tube, having an outer diameter d, wherein said wall is formed from an elastic spring embedded within a biocompatible plastics material, wherein said elastic portion extends from the proximal end for a distance of less than 50% of the length of the hollow elongate body, wherein said elastic portion is adapted such that when said prosthesis is positioned for use within the gastro-intestinal tract said outer surface of said elastic portion contacts said wall of said tract and said inner surface of said elastic portion defines a cylindrical passageway concentric to and within the tract through which fluid compositions flowing within the tract towards the exit end may enter from the proximal end and flow towards and exit the distal end, and b) a flexible portion, comprising a wall having an inner surface and an outer surface that together define a tube having a passageway and consisting of a biocompatible plastics material, joined integrally to and extending from the elastic portion and terminating at the distal end of the hollow elongate tube, wherein said flexible portion is adapted such that when said prosthesis is positioned for use within the gastro-intestinal tract fluid compositions flowing within the cylindrical passageway of the elastic portion towards the exit end of the tract enter the passageway of the flexible portion and flow towards and exit the distal end;

wherein said elastic portion has an outer diameter d which, in its normal undistorted shape, is greater than said diameter of said passageway of said tract at the position in said tract where during use said outer suffice of said wall of elastic portion of said prosthesis contacts said wall of said tract;

wherein said elastic spring in said elastic portion consists of a single helical spring, having two ends and consisting of from 2 to 20 rings, preferably 3 to 20 rings, more preferably 6 to 12 rings, between said ends, wherein each of said rings is concentric with the cylindrical tube of the elastic portion;

and optionally wherein the elastic portion further comprises a layer of biocompatible plastics netting material attached to the outer surface of the wall.

In a second aspect of the present invention, there is provided a prosthesis for use as an anti-reflux device or anti-obesity device within a gastro-intestinal tract of a living organism, said tract comprising an entrance end, an exit end and a wall defining a passageway, of generally circular cross-section having a diameter, along which fluid compositions such as masticated food, digestive secretions and/or mixtures thereof are conveyed within the living organism in a direction towards the exit end of the tract; said prosthesis consisting of a hollow elongate body, having a proximal end and a distal end, wherein said hollow elongate body consists of:

a) an elastic portion having a normal undistorted shape comprising a wall having an inner surface and an outer surface that together define a cylindrical tube, having an outer diameter d, wherein said wall is formed front a plurality of elastic springs embedded within a biocompatible plastics material, wherein said elastic portion extends from the proximal end for a distance of less than 50% of the length of the hollow elongate body, wherein said elastic portion is adapted such that when said prosthesis is positioned for use within the gastro-intestinal net said outer surface of said elastic portion contacts said wall of said tract and said inner surface of said elastic portion defines a cylindrical passageway concentric to and within the tract through which fluid compositions flowing within the tract towards the exit end may enter from the proximal end and flow towards and exit the distal end, and b) a flexible portion, comprising a wall having an inner surface and an outer surface that together define a tube having a passageway and consisting of a biocompatible plastics material, joined integrally to and extending from the elastic portion and terminating at the distal end of the hollow elongate tube, wherein said flexible portion is adapted such that when said prosthesis is positioned for use within the gastro-intestinal tract fluid compositions flowing within the cylindrical passageway of the elastic portion towards the exit end of the tract enter the passageway of the flexible portion and flow towards and exit the distal end;

wherein said elastic portion has an outer diameter d which, in its normal undistorted shape, is greater than said diameter of said passageway of said tract at the position in said tract where during use said outer surface of said wall of elastic portion of said prosthesis contacts said wall of said tract;

wherein said plurality of elastic springs in said elastic portion consists of at least two helical springs, preferably two helical springs, in tandem, each of said helical springs having two ends and consisting of from 1 to 10 rings, preferably 2 to 10 rings, more preferably 3 to 10 rings, between said ends, wherein each of said rings is concentric with the cylindrical tube of the elastic portion, and wherein said springs are formed of the same material;

and optionally wherein the elastic portion further comprises a layer of biocompatible plastics netting material attached to the outer surface of the wall.

Said elastic portion is capable of resuming its normal undistorted shape after removal of a distorting force.

Preferably, said elastic portion is capable of resuming its normal undistorted shape after being subjected to a distorting force of more than 2 Newtons per square millimetre ($Nmm_{-2}$) and less than 20 Newtons per square millimetre ($Nmm^{-2}$).

Preferably, the biocompatible plastics material that is used to form the walls of the elastic portion and flexible portion is an implant grade polymer, which preferably comprises or consists of a silicone polymer. Preferably, the biocompatible plastics netting material is formed of an implant grade polymer, such as a polyester.

Said elastic portion comprises a generally circular cross-section having an outer diameter of a length d which is greater than said diameter of said passage of said tract at the position in said tract where the elastic portion of said prosthesis is to be located during use. More preferably, the length d is such that when positioned for use in the tract said elastic portion exerts a pressure of more than 2 Newtons per square millimetre ($Nmm^{-2}$) and less than 20 Newtons per square millimetre ($Nmm^{-2}$) e.g. 10 $Nmm^{-2}$, on said wall of the tract.

Preferably, when the elastic portion of the prosthesis is in its normal undistorted shape, the diameter of length d is in the range of from 20 mm to 40 mm.

Said elastic portion comprises a wall having an inner surface and an outer surface that together define a cylindrical tube, when in its normal undistorted shape, and the wall is formed from at least one helical elastic spring embedded within a biocompatible plastics material. Preferably, the wall of the cylindrical tube has a thickness in the range from 0.5 mm and 2 mm, i.e. the distance between the between the inner and outer surfaces of the wall is in the range of from 0.5 into to 2 mm.

Preferably, each helical elastic spring, that is/are embedded within said biocompatible plastics material from which the wall of the elastic portion of the prosthesis of the present invention is formed, is made of a metal wire coiled into a helix. Preferably, the wire has a cross-sectional diameter in the range from 0.1 mm to 0.6 mm.

Preferably, each helical elastic spring comprises at least 2 rings, more preferably at least 3 rings. Preferably, successive rings of the or each helical spring are separated by at least 0.1 mm, such as 0.1 to 1 mm, e.g. 0.5 mm.

In the elastic portion of the prosthesis of the present invention, the or each helical spring is completely embedded within the biocompatible material. The ends of each helical spring may be welded to an adjacent ring of the helical spring, so as to reduce the potential for any sharp spring ends perforating the biocompatible material, but this is not essential.

Preferably, said elastic helical spring returns to its normal undistorted shape immediately after removal of a distorting force. Preferably, the elastic helical spring is formed from a metal alloy, more preferably nitinol.

In one embodiment of the present invention, the said elastic portion comprises at least one layer of biocompatible plastics netting material attached to the outer surface of the wall. A preferred biocompatible netting material is polyester. It has been found that the addition of one, two or several layers of netting material can help to maintain the prosthesis in place. It is believed that at least 3 different modes of action may be taking place in a progressive fashion.

1. The external net used alone, creates a rough surface that can avoid slippage of the prosthesis and "rubs" against the mucosa creating friction and reaction of the mucosal wall because of microlesions that the esophageal wall or hiatus hernia wall will attempt to heal if the right pressures are exerted.
2. This process can be significantly enhanced when a few incisions in the mucosa are made so as to cause it to bleed prior to placement of the ring. Blood from the bleeding mucosa seeps into in the netting material and coagulates around the netting fibres and, if more than one layer of netting material is employed, between the layers and adheres the layers together. Then granulation tissue will form breaching at least some of spaces between the outer wall of the elastic portion of the prosthesis and the mucosal wall. This granulation tissue normally retracts into scar tissue that embeds the netting material, and so will attach the prosthesis firmly to the wall but can still be cut endoscopically for removal.
3. Moreover, if staples are used, the net can help block any staples placed either from the outside of the elastic ring or from the inside out.

Surprisingly, it has been found that, when positioned in the hiatus hernia of a mammal, the prosthesis of the present invention is less susceptible to displacement by peristaltic pressures in comparison to a prosthesis comprising a meandering elastic spring, wherein the elastic portion of each prosthesis exerts a similar pressure on the walls of the hiatus hernia. Further, it has been found that users of the prosthesis of the present invention are less susceptible to granulation and ulceration, in comparison to users of the prior art prosthesis that employs a split ring.

In addition, removable or permanent staples may be used in association with the prosthetic of the present invention, in a procedure similar to that disclosed in WO2007/137228.

The second aspect of the present invention is particularly preferred for this embodiment.

Preferably, the living organism is a mammal, more preferably a human.

In a further aspect of the present invention, there is provided an endoscopic procedure for positioning a prosthesis of the present invention in a gastro-intestinal tract of a living organism, wherein said prosthesis includes a layer of biocompatible plastics netting material attached to the outer surface of the wall of the elastic portion, said procedure comprising:
  a. causing or effecting bleeding of the mucosa at the location in the gastro-intestinal tract where said elastic portion of said prosthesis is to be positioned by endoscopic incision,
  b. folding said prosthesis by application of a deforming force to said elastic portion outside of the living organism, thereby to reduce its site from the size of its normal undeformed shape,
  c. whilst maintaining the deforming force, conveying endoscopically said folded prosthesis to the required location in said tract, and
  d. reducing the deforming force under endoscopic control to cause said folded prosthesis to return substantially to its normal undeformed shape, thereby contacting at least a part of the layer of biocompatible plastics netting material with the bleeding mucosa.

In another aspect the present invention, there is provided a method of treatment of reflux disease comprising:
  i) performing esogastroscopy in a patient,
  ii) calibrating the size of the lower esophagus or hiatus hernia,
  iii) selecting a prosthesis of the present invention of appropriate size and comprising a flexible portion adapted for anti-reflux treatment,
  iv) folding the prosthesis and positioning it with introduction forceps over a guide-wire under endoscopic control in the stomach of the patient,
  v) pullback the elastic portion into the lower esophagus or hiatus hernia, and
  vi) releasing the prosthesis in place in the lower esophagus or hiatus hernia with at least a part of the flexible portion remaining in the stomach and optionally,
  vii) placing removable or permanent staples at flexible endoscopy to secure the prosthesis.

In another aspect, the present invention provides a method of reducing obesity in a mammal comprising:
  i) performing esogastroscopy in said mammal,
  ii) calibrating the size of the lower esophagus, hiatus hernia or pre-pyloric antrum,
  iii) selecting a prosthesis of the present invention of appropriate size and comprising a flexible portion adapted for anti-obesity,
  iv) folding the prosthesis and positioning it with introduction forceps over a guide-wire under endoscopic control in the stomach, duodenum or jejunum of the mammal,
  v) pulling back the elastic portion into the lower esophagus, hiatus hernia or pylorus, and
  vi) releasing the prosthesis in place in the lower esophagus, hiatus hernia or pre-pyloric antrum, with at least a part of the flexible portion remaining in the stomach, duodenum and/or jejunum, and, optionally,
  vii) placing movable or permanent staples at flexible endoscopy to secure the prosthesis.

BRIEF DESCRIPTION OF THE DRAWINGS

FIG. 1A is a cross-sectional view of the gastro-intestinal tract including lower esophagus and stomach with no hiatus hernia;

FIG. 2 is a cross-sectional view of the gastro-intestinal tract including lower esophagus and hiatus hernia and showing endoscope and measuring basket;

FIG. 4A is a perspective view of an elastic portion of a prosthesis according to the first aspect of the present invention;

FIG. 4B is a perspective view of an elastic portion of a prosthesis according to the second aspect of the present invention.

FIG. 5A is a view of a helical spring useful in the first aspect of the present invention.

FIG. 5B is a view of 2 helical springs useful in the second aspect of the present invention.

FIG. 8A is a perspective view of the positioning of a prosthesis according to the first aspect of the present invention, with elastic portion located in the hiatus hernia and flexible portion extending into the stomach;

FIG. 8B is a perspective view of the positioning of a prosthesis according to the second aspect of the present invention, with the elastic portion located in the hiatus hernia and flexible portion extending into the stomach with an endoscopic stapler stapling the elastic portion between the helical springs through the stomach wall at the cardia (top of the stomach) with the endoscope in a retroflexed position firing staples.

FIG. 9 is a perspective view of biopsy forceps and sites of bleeding mucosa in the hiatus hernia;

FIG. 10 is a perspective view of the conveyance of a folded prosthesis of the present invention including a layer of netting material attached to the outer surface of the elastic portion in a hiatus hernia including bleeding mucosa;

Figure 1B:
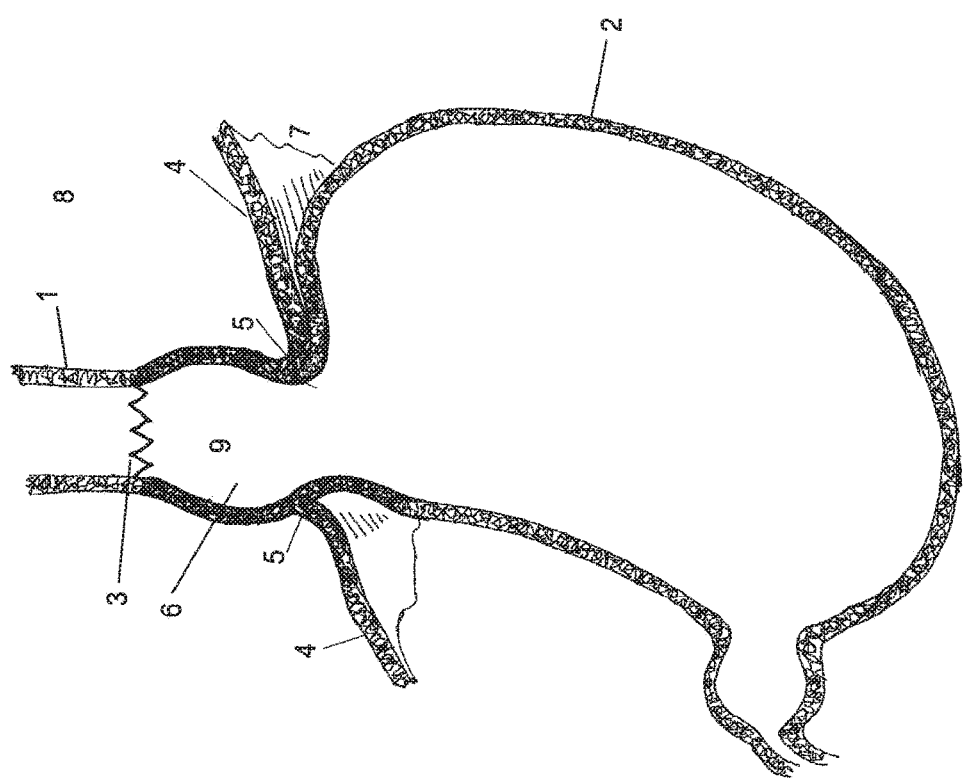
FIG. 1B is a cross-sectional view of the gastro-intestinal tract including lower esophagus, hiatus hernia and stomach.

The invention, in its various aspects, shall now be further described by way of exemplification and with reference to the drawings.

As illustrated in FIG. 1A, the normal lower esophagus (1) and junction with the stomach (2) at the Z line (3) with the location of the diaphragm (4). The lower end of the esophagus passes the hiatus of the diaphragm (5) and meets the upper stomach called the cardia below the hiatus of the diaphragm, so the junction of the esophagus and stomach at the Z line (3) is in the abdominal cavity (7) below the diaphragm (4) and not above the diaphragm in the thorax (8).

FIG. 1B illustrates the lower esophagus (1) and junction with the stomach (2) at the Z (3). The Z line is above the hiatus of the diaphragm (3) because the upper part of the stomach or cardia (6) has moved upwards through the hiatus (5) into the thoracic cavity (8) creating a hiatus hernia (9) that is not present in FIG. 1A. One usually measures the height of the hiatus hernia at endoscopy between the hiatus (5) that causes a narrowing visible from inside the esophagus and the Z line (3). The hiatus hernia (9) can be fixed, that is will not move back down into the abdominal cavity, or it can be sliding, that is it may be mobile and move away from or back down to the abdominal cavity. At the beginning of an endoscopy, or esophago-gastro-duodenoscopy (EGD), the patient has often a gagging reflex that will increase the height of the hiatus hernia but at the end, after examining the stomach and duodenum, when the endoscope is pulled out of the patient, there is less movement and the hernia between the hiatus and Z line is usually measured at the end of the examination with the endoscope, the distances of the standard endoscopes are usually indicated from the tip of the endoscope on the shaft in centimeters.

In FIG. 2, an endoscope (10) is m the esophagus (1) and the calibration basket (12) is passed through the endoscope (10) and opened in the hiatus hernia (9) to measure the diameter of the hiatus hernia.

Figure 3:
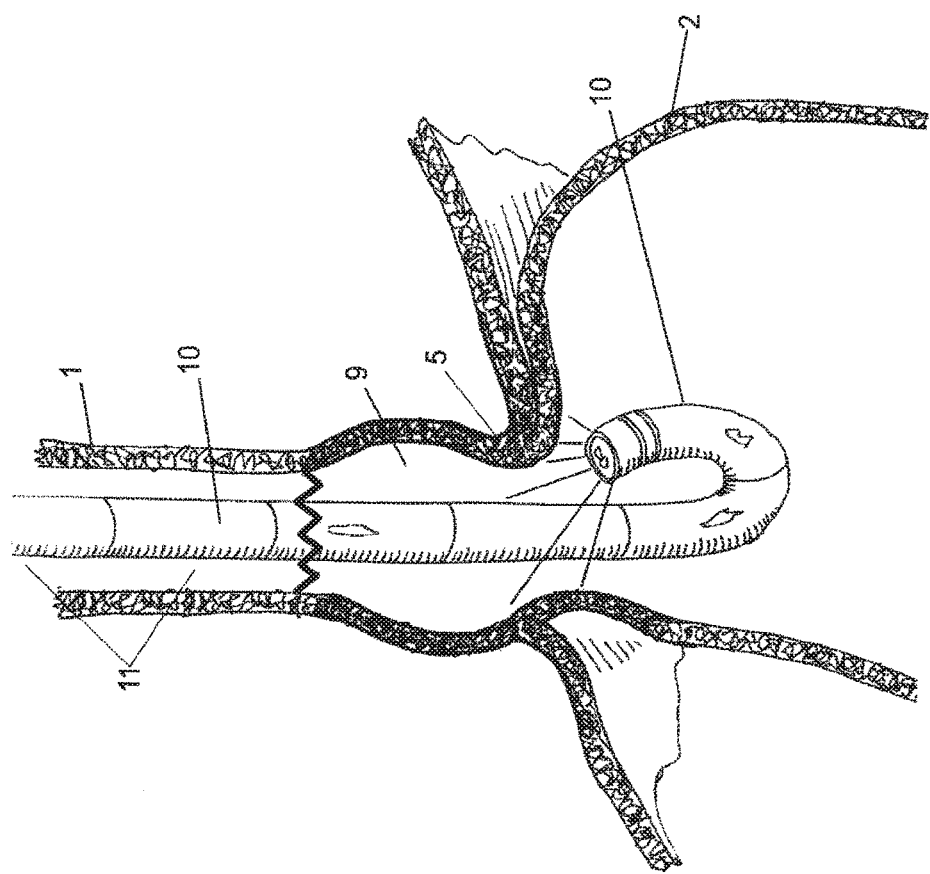
FIG. 3 is a cross-sectional view of the gastro-intestinal tract including lower esophagus and hiatus hernia and showing retroflexed endoscope.

In FIG. 3, the endoscope, gastroscope, (10) is graduated (1), allowing measurement of the height of the hiatus hernia (9). Here the endoscope is passed through the hiatus (5) into the stomach and the tip of the gastroscope (10) is retroflexed. This 180 to 200 degree maneuver allows viewing the hiatus and endoscope passing through the hiatus from below and estimate the width of the hiatus compared to the diameter of the gastroscope. A standard gastroscope is usually slightly less than 10 mm wide. The width of the hiatus seen at retroflexion can be measured and a suitably sized prosthesis selected. For example, if the width of the hiatus is 20 mm, the diameter d of the elastic portion should be selected to slightly exceed the width of the hiatus.

In FIG. 4A, the wall of the elastic portion (13), extending from the proximal end of the prosthesis (14), is made of an implant-grade polymer, e.g. silicone rubber, and has an elastic helical spring (15) molded inside the wall and completely embedded in the polymer material. The rings (18) of the spring (15) are concentric with the wall of the elastic portion (13) and the cylindrical passageway (17), that extends throughout the length of the elastic portion of the prosthesis, through which fluid compositions flowing within the esophagus may enter from the proximal end and flow towards the distal end of the prosthesis.

In FIG. 4B, the elastic portion (13) comprises two separate helical springs (27, 28) in tandem. The top helical spring

(27) is separated from the bottom helical spring (28), leaving a middle part (29) available for stapling.

As shown in FIG. 5A, an elastic helical spring (15) is illustrated with several rings (18). The material of the helical spring is preferably nitinol. The spring is hyperelastic so allowing it to be folded tightly for insertion and resume its normal shape upon release. The diameter of the nitinol thread that forms the spring (15) is between 0.1 to 0.6 mm and the distance between 2 rings (18) is at least 0.5 mm.

In FIG. 5B, there are 2 helical springs, a top one and a bottom one. The distance between 2 rings is about 0.1 mm.

Figure 6B:
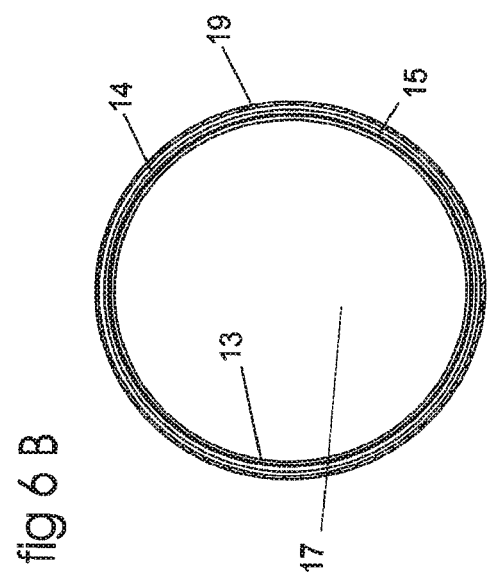
FIG. 6B is a cross sectional view across an elastic portion of a prosthesis of the present invention including a layer of netting material attached to the outer surface.
Figure 6A:
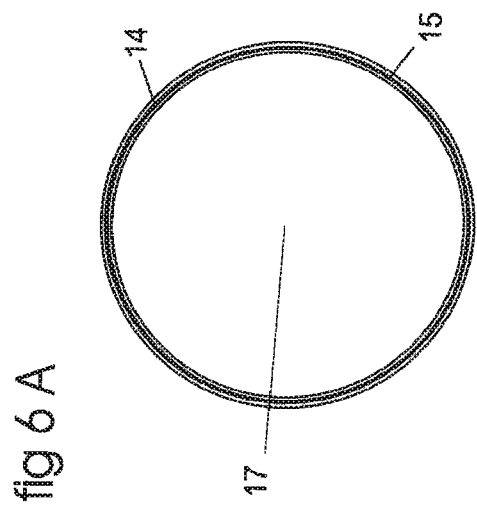
FIG. 6A is a cross sectional view across an elastic portion of a prosthesis of the present invention.

FIG. 6A provides a transverse view of the elastic portion at the proximal end of a prosthesis (14) made of a polymer material, preferably implant grade silicone rubber, with a helical spring (15) embedded within in it. The helical spring (15) insures a cylindrical passageway (17) for food to pass through.

FIG. 6B provides a transverse view of the elastic portion at the proximal end of a prosthesis (14) made of a polymer material, preferably implant grade silicone rubber, with a helical spring (15) embedded within in it. A layer of biocompatible plastics netting material (19), such as polyester, is glued to the outside surface of the elastic portion. The net makes the surface more irregular and helps to hold the prosthesis in its correct position. Additionally, when incisions are made in the hiatus hernia and bleeding is caused before placement of the prosthesis, during the healing process of the incisions and after placement of the prosthesis the blood seeping between the wall of the hiatus hernia and the wall of the elastic portion penetrates the netting material, so helping to create fibrin and collagen bridges between the mucosa of the hiatus hernia and the netting material. The helical spring presses the net covered prosthesis against the bleeding mucosa and, once healed, helps to adhere the prosthesis to the mucosa. In addition, if staples are placed, the net will contribute in securing the staples to the prosthesis.

Figure 7:
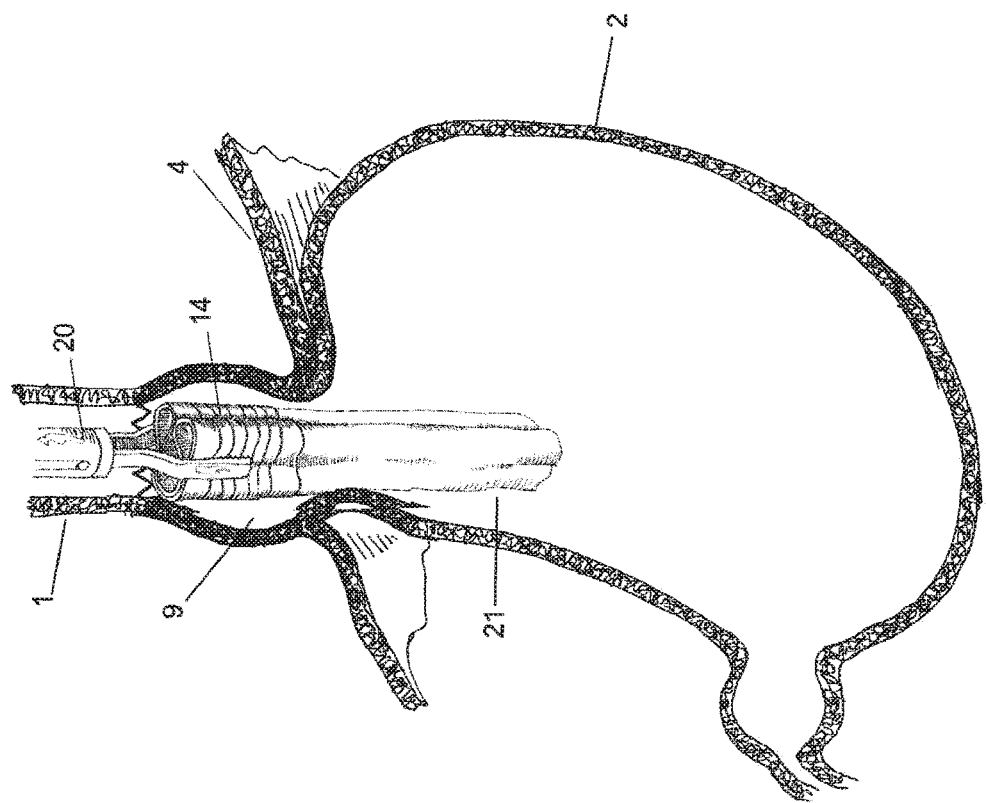
FIG. 7 is a perspective view of the conveyance of a folded prosthesis of the present invention to a hiatus hernia and stomach.

FIGS. 7 and 8 illustrate a procedure for positioning a prosthesis of the present invention in the hiatus hernia.

As shown in FIG. 7, introduction forceps (20) hold the prosthesis tightly folded for conveying the prosthesis into the hiatus, with the flexible portion of the prosthesis (21) provided as either a shorter tube, enabling an anti-reflux valve, or a longer tube, for anti-obesity purposes.

In FIG. 8A, the introduction forceps (20) have released the smooth surfaced prosthesis and are being removed. The elastic portion of the prosthesis (14) is positioned under the Z line (3) but above the hiatus (5) with the flexible portion (21) extending down in to the stomach.

In FIG. 8B, an endoscope (10), with a stapler at the end, is used to staple the prosthesis, having an elastic portion as illustrated in FIG. 4B with the top and bottom springs and the middle portion free of any metal springs to allow stapling of the prosthesis through the elastic portion. The staples (30) are placed through the stomach wall at the fold between the hiatus and the gastric cavity, with the endoscope (10) in a retroflexed position and fired through the tissue and through the wall of the elastic portion of the prosthesis, guided by an ultrasound system placed on the shaft of the endoscope (31). Thereby, one end of a staple is in the elastic portion of the prosthesis and the other end is in the stomach.

Figure 11:
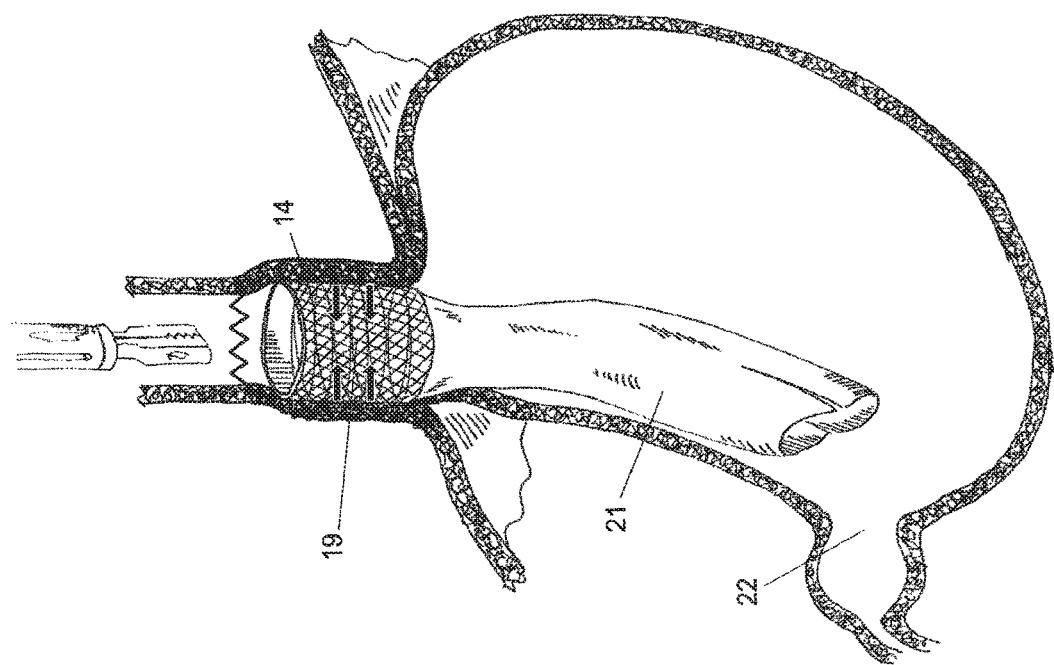
FIG. 11 is a perspective view of the positioning of a prosthesis of the present invention including a layer of netting material attached to the outer surface of the elastic portion, with said elastic portion located in the hiatus hernia and flexible portion extending into the stomach.

FIGS. 9-11 illustrate a procedure for positioning a prosthesis of the present invention that includes a layer of netting material in the hiatus hernia.

In FIG. 9, incisions are made with standard biopsy forceps (24) through the endoscope (10) in the hiatus hernia. The incision sites (25) in the hiatus hernia wall (9) bleed and the patient's blood (26) covers the mucosa.

In FIG. 10, whilst the incisions are still bleeding, the introduction forceps (20) convey the prosthesis, including a layer of netting material (19), with the proximal end located in the hiatus hernia and the distal end in the stomach.

In FIG. 11, the introduction forceps (20) have released the prosthesis and are being removed. The elastic portion of the prosthesis resumes its normal undistorted shape after release from the forceps and is positioned under the Z line (3) but above the hiatus (5) in the hiatus hernia. The elastic portion, having a diameter slightly larger than the diameter of the hiatus, tightly abuts against the walls of the bleeding mucosa, and the blood from the wall penetrates the netting material (as represented by the arrows). When the blood coagulates and scarring occurs, fibrin and collagen bridges help to hold the elastic portion of the prosthesis in the hernia. The flexible portion (21) in this particular embodiment is shown to be longer in the stomach and, in some embodiments, may reach through to the pylorus (22) into the duodenum and small bowel, not shown in this drawing. As the fixation of the prosthesis in the hernia is stronger with a netting material than without, the better adhesion of the prosthesis to the hiatus hernia wall enables longer, heavier flexible portions that can extend well beyond the stomach. In addition, staples, permanent or resorbable, can be placed as shown in FIG. 8B.

Figure 12:
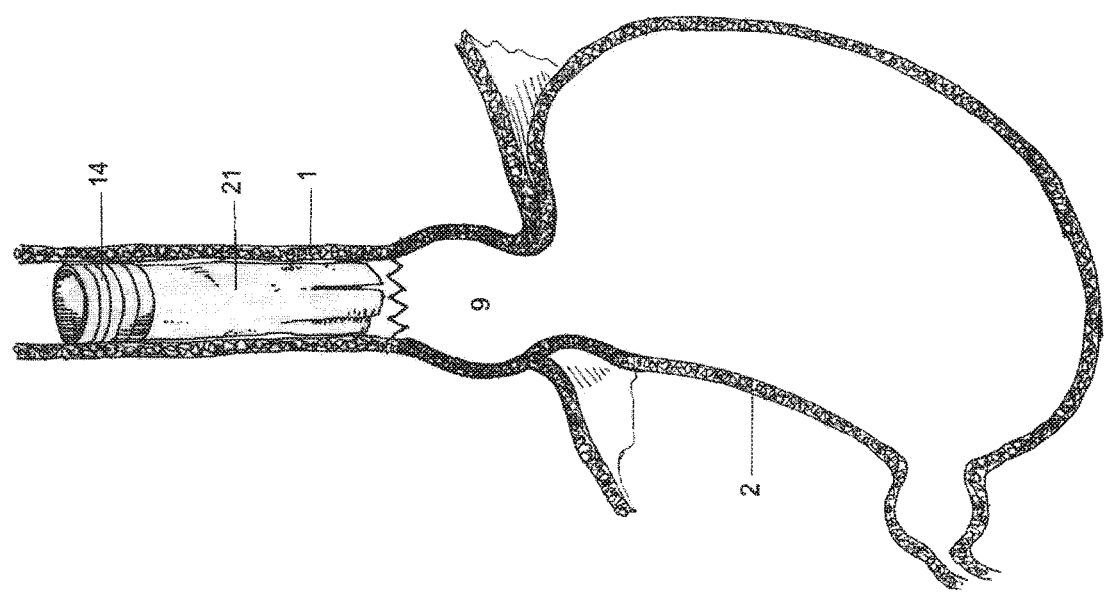
FIG. 12 is a perspective view of the positioning of a prosthesis of the present invention located in the lower esophagus.
Figure 13:
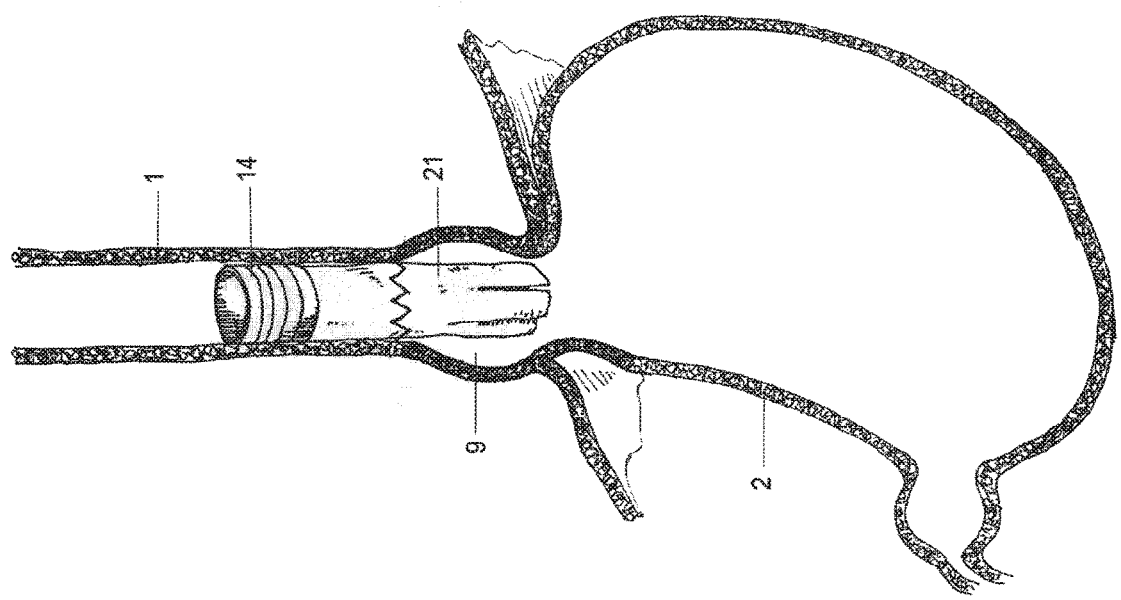
FIG. 13 is a perspective view of the positioning of a prosthesis of the present with said elastic portion located in the lower esophagus and flexible portion extending into the hiatus hernia.
Figure 14:
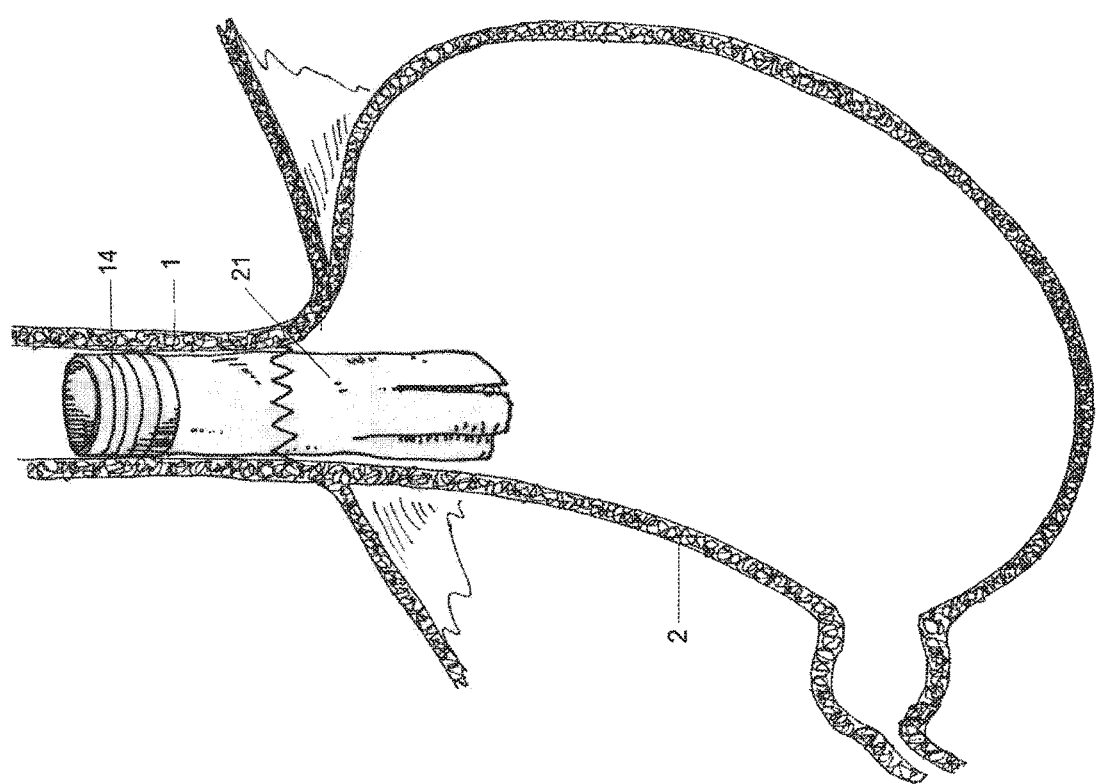
FIG. 14 is a perspective view of the positioning of a prosthesis of the present invention with said elastic portion located in the lower esophagus and flexible portion extending into the stomach, in the absence of a hiatus hernia.

FIGS. 12-14 illustrate the prosthesis of the present invention positioned at various locations within the gastro-intestinal tract.

Figure 15:
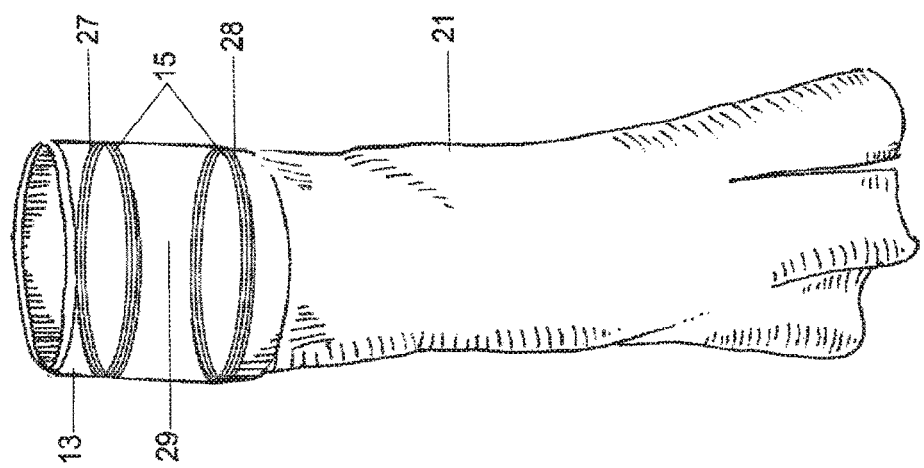
FIG. 15 is a perspective view of a prosthesis according to the second aspect of the present invention having two separate helical springs in tandem.

FIG. 15 shows perspective view of a prosthesis according to the second aspect of the present invention. The elastic portion of the prosthesis (13) comprises two separate helical springs (15) in tandem, the top spring (27), the bottom spring (28) and an intermediate portion (29) between the springs available for stapling. The region of the elastic portion between the helical springs may provide an area for stapling the elastic portion to the wall of the gastro-intestinal tract. If staples are used, they are preferably removable staples, such as are disclosed in WO2007/137228 or staples placed with an endoscopic stapler as the one developed by Medigus Ltd where the staples are placed with a retroflexed position of the endoscope. The staples can be non-resorbable, or resorbable if the device is to be removed and exchanged after a period of time. Non-resorbable staples can be removed mechanically if necessary.

In one embodiment of the present invention, a prosthesis can be made essentially from an implant-grade polymer tube having embedded within it towards one end at least one helical elastic spring. The prosthesis has dimensions such that, in use, it exerts pressures on the gastro-intestinal wall or hiatus hernia wall that are strong enough to retain the prosthesis in place and avoid migration but not exert pressures constantly in one location of the tract that can lead to the creation of lesions, such as ulcerations that may bleed, or proliferation of granulation tissue of the underlying mucosa.

The longer prostheses can be used as obesity tubes, which cause satiety because these tubes force the patient to eat smaller mouthfuls, chew their food longer and thereby help patients develop earlier satiety when eating so they can eat less without being hungry and therefore help them lose weight. The lower ends of the obesity tubes can reach at different lengths into the stomach or can pass the pylorus and reach the duodenum and/or jejunum to cause malabsorption used in addition to a diet to help patient lose weight and thereby contribute to control the obesity epidemic seen worldwide.

It is well known as reviewed in the article: "The Association Between Obesity and GERD: a Review of the Epidemiological Evidence" by Hashem El-Serag in Digestive Disease and Science in the September 2008 issue, volume 53(9): 2307-2312 that increased body mass index (BMI) increases the incidence of GERD, so GERD and obesity could be treated in patients suffering from GERD and obesity with one single device helping these patients lose weight and decrease or eliminate their GERD symptoms after removal of the device once they have lost some weight.

An ideal prosthesis has to be strong enough to resist peristaltic pressures and stay in position for a certain amount of time but flexible enough to be folded sufficiently tightly to be passed through the mouth, open upon release position with the flexible portion of the prosthesis terminating at the distal end in the stomach, or beyond, and the elastic portion of the prosthesis located in the hernia or lower esophagus. The prosthesis has to avoid migration if too soft or ulcerations, perforation or granulation tissue formation if too hard, if necessary using staples as well to avoid migration. The prosthesis of the present invention is particularly suitable for use with fixed sliding hiatus hernias (as opposed to rolling or mixed sliding and rolling hiatus hernias) that measure anywhere between 1 cm and 6 cm in height as measured by the graduations present on all standard gastroscopes, and 20 mm to 40 mm in width.

Preferably, each helical spring is made of a hyperelastic material such as nitinol. The diameter of the nitinol thread is preferably from 0.1 mm to 0.5 mm, but more preferably from 0.2 mm to 0.4 mm. Each spring preferably consists of anywhere between 2 and 20 rings, but more preferably 6 to 12 rings.

Each helical spring is completely embedded inside a biocompatible polymer, preferably an implant-grade polymer, and is preferably made of silicone polymer. The thickness of the wall of the elastic portion of the prosthesis in which the helical spring is embedded is from 0.5 mm to 2 mm. The prosthesis may be folded and held tightly with an introductory forceps (see FIG. 7) e.g. over a guide-wire placed at prior gastroscopy, that introduces the whole prosthesis in the stomach, then the folded prosthesis is pulled back into the hernia leaving the flexible portion, that enables the anti-reflux or obesity action, in the stomach. The introductory forceps are opened and the elastic portion of the prosthesis is released in the hiatus hernia (FIG. 8)

The advantage of a prosthesis of the present invention, is that any lateral pressure exerted on the helical spring will exert an equivalent back-pressure rather than collapse like the meandering spring employed in the prior art prosthesis. Also, by having spaces between and flexibility in the rings of the helical spring, the mucosa in contact with the elastic portion of the prosthesis can tolerate the prosthesis much better than when a split-ring is used, as it believed that the split-ring exerts a uniform strong pressure on the mucosa which interferes more with the blood flow in the wall of the hernia.

The prosthesis of the present invention may stay for a certain amount of time in position in the gastro-intestinal tract without causing significant lesions, and may be removed endoscopically through the mouth by using a strong metal loop that is tightened progressively around the prosthesis to collapse it.

Preferably, the elastic portion will resume its normal undistorted shape after being subjected to a distorting force of more than 2 $N/mm^2$ and less than 20 $N/mm^2$. Objectively, the difference can be measured simply by using a measuring system where a dynamometer (as manufactured by Pesola of Switzerland for example) is used to pull with a little hook the elastic portion of the prosthesis placed horizontally on a hard surface (end of a table) and by exerting a pressure on the outside of the prosthesis until the inside part where the pressure is exerted touches the other inside part on the opposite side. The pressure needed to have one side touch the other opposite side is called the collapsing pressure.

The helical spring will preferably need from 2 $N/mm^2$ to 20 $N/mm^2$ pressure exerted on it for one end (16) to touch the other end (16) of the spring, more preferably from 4 $N/mm^2$ to 8 $N/mm^2$ pressure range which is the best compromise for the prosthesis to stay in position in a fixed hiatus hernia.

Preferably, the diameter d of the elastic portion of the prosthesis is such that when positioned in the gastro-intestinal tract and in its normal undistorted shape it exerts a pressure of no less than 2 $N/mm^2$ and no more than 20 $N/mm^2$ on the mucosal wall. If the pressure is significantly less than 2 $N/mm^2$ then the prosthesis may become dislodged from its correct position. If the pressure is significantly more than 20 $N/mm^2$, then the mucosa may become damaged after implantation.

The diameter of the thread of a helical nitinol spring is preferably between 0.1 mm and 0.6 mm, more preferably between 0.2 mm and 0.5 mm.

Typically, any prosthesis of the invention exerting a pressure of 2 $N/mm^2$ to 20 $N/mm^2$ on the wall of the gastro-intestinal tract will have the qualities needed to remain in a hiatus hernia if the hiatus hernia is fixed, is higher than 1 cm high, is more than 20 mm wide and has a hiatus of less than 20 mm through the opening in the diaphragm separating the hernia above and the gastric cavity underneath the hiatus. The prosthesis can also be placed in the lower esophagus of a patient with no hiatal hernia, but it preferably has a diameter d at least 2 to 4 mm wider than the estimated size of the diameter of the esophagus passageway.

The prosthesis may be used as an anti-reflux device and can be used in several clinical conditions, these examples are not being exhaustive as other situations can be considered. For example, the anti-reflux device can be used to determine if a patient taking constant medication (most often proton pump inhibitors or PPIs) could be a good candidate for a mechanical solution as provided by surgery, the most common operation being the Nissen fundoplication. The Diagnostic GARD normally without the outside net as in the first aspect of the invention with one helical spring can be placed if the conditions above are fulfilled to determine if a patient will be improved by placing the GARD Diagnostic device without an outside net and determine if the patient can be weaned of PPIs. If so, the device can be removed before surgery and the operation performed or preferably the Diagnostic GARD can be replaced by a Therapeutic GARD as described in the second aspect of the invention with a net, incisions are then performed to make the mucosa bleed and if necessary staples are placed.

Another condition, where the GARD can be used is refractory GERD that is a common condition seen by gastroenterologists where patients who have GERD have already been prescribed PPIs and do not respond to therapy even when the dosages of PPIs are increased. This situation can be caused by non acid reflux such as bile reflux, patients with an hypersensitive esophagus that feel even small volumes of refluxate or other conditions not related to reflux such as esophageal motor disorders. It is usually common to endoscope these patients and take biopsies to rule out eosinophilic esophagitis and perform either an esophageal 24 or 48 hour pH measurement study to determine if there is acid reflux or a ph-impedance test that can be done to determine if there is non acidic (bile) reflux. The Diagnostic GARD can block all reflux from the stomach into the esophagus: acid, that is strong acid or weak acid reflux and bile which is alkaline and can be placed for a few days or a few weeks to determine if the symptoms improve. If the symptoms improve, again the Diagnostic GARD can be replaced by a Therapeutic GARD as described in the second aspect of the invention with a net, biopsies are then performed to make the mucosa bleed and if necessary staples are placed.

One common situation is when an overweight or obese patient with body mass indexes (BMI of 25 to 35) has GERD or Gastro-Esophageal Reflux Disease. This device called the OB GARD can be placed in the lower esophagus or hiatus hernia of these patients and with dietetic counseling, the longer tubular device such as in FIG. 11 will block reflux but also slow down the passage of food from the esophagus into the stomach forcing patients to eat more slowly, chew their food longer and this will help induce earlier satiety and help patients lose weight. When the GARD is removed after a few months, the patient can be expected to have lost 10 kg or more which will decrease his/her GERD symptoms and help them decrease or stop the often life-long medication taken for GERD. This application is completely novel as treatments for GERD exist, mainly drugs such a proton pump inhibitors or devices to treat obesity such a gastric bands also but there are no devices placed through the mouth and removed through the mouth on an ambulatory basis that can help patients who are overweight or obese and have GERD lose some weight to improve their GERD symptoms by helping them lose weight. Gastric bands used to treat obesity tend to increase the patient's GERD symptoms, not decrease them.

A prosthesis having a longer flexible portion extending into the stomach close to the antrum or pylorus can help patients lose weight by mechanisms similar to the vertical sleeve gastrectomy, an operation done for morbid obesity. This operation has now been demonstrated as helping obese patients lose significant weight as demonstrated in the recent article by Gluck B et al in *Obes Surg.* 2011 August; 21(8):1168-71: "Laparoscopic sleeve gastrectomy is a safe and effective bariatric procedure for the lower BMI (35.0-43.0 kg/m2) population".

The OB tube works almost like a sleeve gastrectomy but part of the stomach is not removed. The device can be placed and removed on an ambulatory basis through endoscopic placement through the mouth without general anesthesia. The device will help overweight patients or moderately obese patients with a BMI between 25 and 40 lose weight and therefore control complications linked to excess weight or obesity such as diabetes among others.

In addition, a polyester net (19) in FIG. 6B can be glued on the outside surface of the elastic portion. This net can help create adhesion of the ring with the mucosa of the lower esophagus or hernia. One way to improve adhesion and prevent slippage of the ring in the stomach is, after calibration to determine the size has been performed as described here above, to make standard incisions through the endoscope the mucosa underlying where the elastic portion of the prosthesis will be located in the hiatus hernia or in the lower esophagus before placing the prosthesis in the esophagus or hiatus hernia. Typically, from 4 to 10 incisions are made in a circular manner around the mucosa. The incisions will cause slight bleeding and once the elastic portion with an e.g. polyester net is placed in position immediately after the biopsies are taken, the blood in contact between the mucosa and the net will coagulate and create fibrin bridges and collagen scarring helping adhesion of the prosthesis to the mucosa. Alternatively, medication that induces fibrosis can be incorporated in the prosthesis to cause or improve adhesion or staples can be placed to secure the ring in place.

The prosthesis may be removed from its fitted position by passing a closed loop through the working channel of the endoscope, the strong metal loop is then opened under endoscopic control and the elastic portion of the prosthesis is snared and the loop tightened so that the prosthesis resumes the folded position used for placement. The prosthesis is then removed safely out of the patient. If necessary, any adhesions present between the device and the mucosa can be out endoscopically and staples removed.

Whilst the invention has been described in detail and several embodiments have been illustrated, other embodiments, alternatives and modifications should become apparent to those skilled in the art without departing from the spirit and scope of the invention.

The invention claimed is:

1. A prosthesis for use as an anti-reflux device or anti-obesity device within a gastro-intestinal tract of a living organism, said tract comprising an entrance end, an exit end and a wall defining a passageway, of generally circular cross-section having a diameter, along which fluid compositions such as masticated food, digestive secretions and/or mixtures thereof are conveyed within the living organism in a direction towards the exit end of the tract; said prosthesis consisting of a hollow elongate body, having a proximal end and a distal end, wherein said hollow elongate body consists of:

a) an elastic portion having a normal undistorted shape comprising a wall having an inner surface and an outer surface that together define a cylindrical tube, having an outer diameter d, wherein said wall is formed from a plurality of elastic springs embedded within a biocompatible plastics material, wherein said elastic portion extends from the proximal end for a distance of less than 50% of the length of the hollow elongate body, wherein said elastic portion is adapted such that when said prosthesis is positioned for use within the gastro-intestinal tract said outer surface of said elastic portion contacts said wall of said tract and said inner surface of said elastic portion defines a cylindrical passageway concentric to and within the tract through which fluid compositions flowing within the tract towards the exit end may enter from the proximal end and flow towards and exit the distal end, and b) a flexible portion, comprising a wall having an inner surface and an outer surface that together define a tube having a passageway and consisting of a biocompatible plastics material, joined integrally to and extending from the elastic portion and terminating at the distal end of the hollow elongate tube, wherein said flexible portion is adapted such that when said prosthesis is positioned for use within the gastro-intestinal tract fluid compositions flowing within the cylindrical passageway of the elastic portion towards the exit end of the tract enter the passageway of the flexible portion and flow towards and exit the distal end;

wherein said elastic portion has an outer diameter d which, in its normal undistorted shape, is greater than said diameter of said passageway of said tract at the position in said tract where during use said outer surface of said wall of elastic portion of said prosthesis contacts said wall of said tract;

wherein said plurality of elastic springs in said elastic portion consists of at least two helical springs in tandem, each of said helical springs having two ends and consisting of from 1 to 10 rings between said ends, wherein each of said rings is concentric with the cylindrical tube of the elastic portion, and wherein said springs are formed of the same material;

wherein the elastic portion further comprises a layer of biocompatible plastics netting material adapted to cause bleeding of the mucosa, attached to the outer surface of the wall.

2. The prosthesis of claim 1, wherein said elastic portion is capable of resuming its normal undistorted shape after being subjected to a distorting force of more than 2 Newtons per square millimetre ($Nmm^{-2}$) and less than 20 $Nmm^{-2}$.

3. The prosthesis of claim 1, wherein said biocompatible plastics material used to form the walls of the elastic portion and flexible portion comprises or consists of a silicone polymer.

4. The prosthesis of claim 1, wherein the diameter d is from 20 mm to 40 mm.

5. The prosthesis of claim 1, wherein said wall of said elastic portion has a thickness between the inner and outer surfaces of from 0.5 mm to 2 mm.

6. The prosthesis according to claim 1, wherein said helical springs are made of a metal wire having a cross-sectional diameter in the range from 0.1 mm to 0.6 mm.

7. The prosthesis as claimed in claim 1, wherein said helical springs and said optional connecting member if present are made of metal wire having a cross-sectional diameter in the range from 0.1 mm to 0.6 mm.

8. A prosthesis of claim 1, wherein successive rings of the helical springs are separated by at least 0.1 mm.

9. An endoscopic procedure for positioning the prosthesis of claim 1, in a gastro-intestinal tract of a living organism, wherein said prosthesis includes a layer of biocompatible plastics netting material attached to the outer surface of the wall, said procedure comprising:
 a. causing or effecting bleeding of the mucosa at the location in the gastro-intestinal tract where said elastic portion of said prosthesis is to be positioned by endoscopic incision,
 b. folding said prosthesis by application of a deforming force to said elastic portion outside of the living organism, thereby to reduce its size from the size of its normal undeformed shape,
 c. whilst maintaining the deforming force, conveying endoscopically said folded prosthesis to the required location in said tract, and
 d. reducing the deforming force under endoscopic control to cause said folded prosthesis to return substantially to its normal undeformed shape, thereby contacting at least a part of the layer of biocompatible plastics netting material with the bleeding mucosa.

10. A method of treatment of reflux disease comprising:
 i) performing esogastroscopy in a patient,
 ii) calibrating the size of the lower esophagus or hiatus hernia,
 iii) selecting the prosthesis according to claim 1 of appropriate size and comprising a flexible portion adapted for anti-reflux treatment,
 iv) folding the prosthesis and positioning the prothesis with forceps over a guide-wire under endoscopic control in the stomach of the patient,
 v) pulling back the elastic portion into the lower esophagus or hiatus hernia, and
 vi) releasing the prosthesis in place in the lower esophagus or hiatus hernia with at least a part of the flexible portion remaining in the stomach.

11. A method of reducing obesity in a mammal comprising:
 i) performing esogastroscopy in said mammal,
 ii) calibrating the size of the lower esophagus, hiatus hernia or pre-pyloric antrum,
 iii) selecting the prosthesis according to claim 1, of appropriate size and comprising a flexible portion adapted for anti-obesity,
 iv) folding the prosthesis and positioning the prosthesis with forceps over a guide-wire under endoscopic control in the stomach, duodenum or jejunum of the mammal,
 v) pulling back the elastic portion into the lower esophagus, hiatus hernia or pylorus, and
 vi) releasing the prosthesis in place in the lower esophagus, hiatus hernia or pre-pyloric antrum, with at least a part of the flexible portion remaining in the stomach, duodenum and/or jejunum.

\* \* \* \* \*